(12) United States Patent
Nagai (10) Patent No.: US 9,837,178 B2
(45) Date of Patent: Dec. 5, 2017

(54) IMAGE PROCESSING APPARATUS, IMAGING SYSTEM, AND IMAGE PROCESSING METHOD

(71) Applicant: CANON KABUSHIKI KAISHA, Tokyo (JP)

(72) Inventor: Kentaro Nagai, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/200,256

(22) Filed: Jul. 1, 2016

(65) Prior Publication Data

US 2017/0023683 A1    Jan. 26, 2017

(30) Foreign Application Priority Data

Jul. 22, 2015    (JP) ................. 2015-145042

(51) Int. Cl.

| | |
|---|---|
| *G01T 1/24* | (2006.01) |
| *G21K 1/06* | (2006.01) |
| *G06T 5/20* | (2006.01) |
| *A61B 6/00* | (2006.01) |

(52) U.S. Cl.
CPC ............. *G21K 1/06* (2013.01); *A61B 6/484* (2013.01); *A61B 6/5258* (2013.01); *A61B 6/542* (2013.01); *G06T 5/20* (2013.01)

(58) Field of Classification Search
CPC .......... G06T 5/20; G06T 2200/04; G06T 2207/20192; G06T 2207/20024; G06T 7/0085; G06T 2207/10104; G06T 2207/10116; G01T 1/2985; G01T 1/247; G21K 1/06

USPC .................................. 250/370.09
See application file for complete search history.

(56) References Cited

U.S. PATENT DOCUMENTS

| | | | | |
|---|---|---|---|---|
| 7,623,732 | B1 * | 11/2009 | Thieret .............. | G06F 17/15 358/3.26 |
| 8,855,394 | B2 * | 10/2014 | Yang ................ | G06K 9/40 382/131 |
| 2002/0071600 | A1 * | 6/2002 | Yamada ............. | G06T 5/004 382/132 |
| 2006/0018526 | A1 * | 1/2006 | Avinash ............ | G06T 5/50 382/132 |

(Continued)

FOREIGN PATENT DOCUMENTS

WO    2010/034968 A1    4/2010

*Primary Examiner* — Taeho Jo
(74) *Attorney, Agent, or Firm* — Fitzpatrick, Cella, Harper & Scinto (57) ABSTRACT

An image processing apparatus includes: a measurement data acquiring unit that acquires data obtained by using an imaging apparatus to capture an image formed by an electromagnetic wave transmitted through an object, as measurement data of the object; an image generating unit that generates a first image and a second image that represent information on different physical quantities, from the measurement data; a filter characteristics determining unit that determines, based on the first image, filter characteristics to be set when an anisotropic filter is applied, for each position in the image; and a filtering unit that applies the anisotropic filter to the second image while varying the filter characteristics of the anisotropic filter for each position in the image in accordance with the filter characteristics determined based on the first image.

15 Claims, 7 Drawing Sheets

(56) References Cited

U.S. PATENT DOCUMENTS

| | | | |
|---|---|---|---|
| 2006/0093194 A1* | 5/2006 | Grady | G06T 5/002 382/128 |
| 2006/0133564 A1* | 6/2006 | Langan | G01N 23/046 378/8 |
| 2007/0035706 A1* | 2/2007 | Margulis | G03B 21/20 353/122 |
| 2008/0007747 A1* | 1/2008 | Chinen | G06T 5/002 358/1.9 |
| 2008/0123912 A1* | 5/2008 | Lal | G06T 7/194 382/128 |
| 2009/0232269 A1* | 9/2009 | Hsieh | A61B 6/032 378/5 |
| 2010/0027906 A1* | 2/2010 | Hara | G06T 7/13 382/264 |
| 2010/0228129 A1* | 9/2010 | Osumi | A61B 8/14 600/443 |
| 2010/0259650 A1* | 10/2010 | Sasaki | G06K 9/6212 348/241 |
| 2010/0303338 A1* | 12/2010 | Stojancic | G06K 9/00744 382/154 |
| 2011/0069875 A1* | 3/2011 | Goto | A61B 6/032 382/131 |
| 2011/0158498 A1* | 6/2011 | Li | G06T 11/008 382/132 |
| 2012/0039518 A1* | 2/2012 | Bruder | A61B 6/032 382/131 |
| 2012/0078104 A1* | 3/2012 | Osumi | A61B 8/5215 600/443 |
| 2013/0032727 A1* | 2/2013 | Kondoh | G01N 23/046 250/394 |
| 2014/0010473 A1* | 1/2014 | Basu | G06T 11/008 382/264 |
| 2014/0056497 A1* | 2/2014 | Hsieh | G06T 5/005 382/131 |
| 2014/0126690 A1* | 5/2014 | Yamaguchi | A61B 6/484 378/36 |
| 2014/0153692 A1 | 6/2014 | Larkin et al. | |
| 2014/0314333 A1* | 10/2014 | Takahashi | A61B 6/5258 382/264 |
| 2015/0269711 A1* | 9/2015 | Ohishi | G06T 5/002 382/132 |
| 2015/0279027 A1 | 10/2015 | Nagai | |

* cited by examiner

FIG. 7A THEORETICAL VALUES
 FIG. 7B COMPARATIVE EXAMPLE 1
 FIG. 7C COMPARATIVE EXAMPLE 2
 FIG. 7D EMBODIMENT

FIG. 8

IMAGE PROCESSING APPARATUS, IMAGING SYSTEM, AND IMAGE PROCESSING METHOD

BACKGROUND OF THE INVENTION

Field of the Invention

The present invention relates to an image processing technique for an object image.

Description of the Related Art

Measuring methods using a phase as means for precisely measuring substances have been conventionally used. Measuring methods using a phase involve causing interference with (coherent) incident light that has aligned wave fronts and measuring resultant interference fringes to determine a change in incident light wave front (phase) due to a phase difference equal to one severalth to one several-tenth of the wavelength. An interferometer using such a measuring method is suitable means for measuring, for example, slight concaves and convexes on a surface of a lens.

Among the wave front measuring methods using interference, attention has recently been paid to an X-ray phase imaging utilizing light (electromagnetic waves) with a wavelength of several tens of nanometers or shorter, that is, X rays. Unlike X-ray absorption imaging in which contrast resulting from absorption by an object is imaged, the X-ray phase imaging involves detecting, based on phase interference, a change in the length of an optical path of incident light formed during transmission of X rays through the object.

As an example of the X-ray phase imaging, Talbot interferometry using X rays will be described. In an X-ray Talbot interferometer, X rays from a light source are transmitted through an object to change an incident phase of light. Light transmitted through the object is diffracted by a grating referred to as a diffraction grating and having a periodic pattern, to form a first interference pattern at a position located at a predetermined distance referred to as a Talbot length, from the diffraction grating. A change in the first interference pattern in this case is analyzed through a comparison with a change in the first interference pattern in a case where the object is not present, to determine a change in incident light wave front.

The pattern period of the diffraction grating with the periodic pattern as described above varies according to conditions such as the length of the apparatus and the wavelength of the incident light. Typical X rays have a period of the order of several micrometers. As is known, the first interference pattern formed by the X rays also has a period of the order of several micrometers. In such a case, common detectors have a resolution of at most several tens of micrometers and thus fail to detect the first interference pattern. Thus, a shield grating having substantially the same period as that of the first interference pattern is arranged at a position where the interference pattern is formed. The shield grating blocks a portion of the first interference pattern to form a second interference pattern with a period of approximately several hundred micrometers, that is, a moiré pattern. Then, the moiré pattern is detected by a detector to allow a change in the interference pattern to be indirectly measured. Examples of a method for forming a moiré pattern include a method of aligning the direction of the shield grating with the period adjusted with the direction of the first interference pattern formed by the first grating (enlarged moiré pattern) and a method of rotating the grating to adjust the period and direction of the moiré pattern (rotated moiré pattern).

Numerical analysis of the moiré pattern allows several parameters relating to the object to be acquired. In a typical example of parameter acquisition, a difference in the length of the optical path of the incident light is detected as a differential phase. This allows the refractive index for the object to be calculated. Such images based on the refractive index advantageously exhibit a higher signal-to-noise ratio (SN ratio) than X-ray absorption images particularly for some types of objects such as soft tissues and plastics.

In recent years, studies have been conducted on techniques for acquiring information on a small-angle scattering of not more than the order of pixels for the object by calculating a change in the amplitude of the moiré pattern. In other words, a two-dimensional X-ray Talbot interferometer allows, in addition to the conventional absorption image, images representing independent physical quantities such as a differential phase image, an amplitude image, and a scattering image to be acquired during one imaging process.

Moreover, in recent years, two-dimensional X-ray Talbot interferometers including a two-dimensional grating have been actively studied. The two-dimensional X-ray Talbot interferometers are characterized by, for example, being capable of simultaneously acquiring a differential image in an X axis direction and a differential image in a Y axis direction that is perpendicular to the X axis. The two-dimensional X-ray Talbot interferometers can thus acquire more accurate refractive-index information. In US Patent Application Publication No. US 2014/0153692, a method is disclosed in which a clear image of the object is acquired from such differential phase images in the two directions as described above. The method in US Patent Application Publication No. US 2014/0153692 enables an edge boundary of the object to be clarified utilizing inverse Riesz transform and is expected to further enhance the SN ratio for the contour of the object. Alternatively, the Laplacian may be determined by further differentiating differential phases.

Such techniques are very effective for modalities such as X-ray interferometers which use X rays, particularly when the object is susceptible to exposure such as a living organism. For such objects, an X-ray exposure dose is desirably as low as possible. Naturally, a trade-off exists between a reduction in exposure dose and a decrease in SN ratio, and a technique is desired which emphasizes the edge more significantly for the final image.

A technique for effectively emphasizing the edge is disclosed in, for example, International Publication No. WO 2010/034968. The technique in International Publication No. WO 2010/034968 is an improved technique for noise reduction that enables emphasis only of an information portion desired to be effectively emphasized by repeating a process of applying an anisotropic noise reduction filter in accordance with the location and shape of the object. Such a technique can be applied to the X-ray Talbot interferometer. However, the technique in International Publication No. WO 2010/034968 needs to pre-achieve a given SN ratio for an image obtained as primary information so that the direction of the anisotropic filter can be detected. On the other hand, when the exposure is reduced as much as possible for the purpose of less exposure, the SN ratio may decrease to such a degree that the technique in International Publication No. WO 2010/034968 is difficult to apply (a degree that the direction of the anisotropic filter cannot be detected).

One of such examples is imaging of a cartilage in the living organism. The cartilage cannot be imaged by conventional absorbed X rays and is one of imaging targets to which the X-ray Talbot interferometer is expected to be applied. The cartilage itself exhibits a high refractive index in vacuum. However, the cartilage present in a living tissue exhibits a lower relative refractive index between this living tissue and another living tissue, preventing a sufficient contrast from being achieved, though imaging is possible.

SUMMARY OF THE INVENTION

With the above-described circumstances in view, an object of the present invention is to provide a technique that allows reliable filter effects to be exerted when anisotropic filtering is applied to an object image (particularly an image with a low SN ratio).

The present invention in its first aspect provides an image processing apparatus comprising: a measurement data acquiring unit that acquires data obtained by using an imaging apparatus to capture an image formed by an electromagnetic wave transmitted through an object, as measurement data of the object; an image generating unit that generates a first image and a second image that represent information on different physical quantities, from the measurement data; a filter characteristics determining unit that determines, based on the first image, filter characteristics to be set when an anisotropic filter is applied, for each position in the image; and a filtering unit that applies the anisotropic filter to the second image while varying the filter characteristics of the anisotropic filter for each position in the image in accordance with the filter characteristics determined based on the first image.

The present invention in its second aspect provides an imaging system comprising: an imaging apparatus that captures an image formed by an electromagnetic wave transmitted through an object to output measurement data of the object; and the image processing apparatus that applies image processing to the measurement data obtained by the imaging apparatus.

The present invention in its third aspect provides an image processing method comprising the steps of: causing a computer to acquire data obtained by using an imaging apparatus to capture an image formed by an electromagnetic wave transmitted through an object, as measurement data of the object; causing the computer to generate a first image and a second image that represent information on different physical quantities, from the measurement data; causing the computer to determine, based on the first image, filter characteristics to be set when an anisotropic filter is applied, for each position in the image; and causing the computer to apply the anisotropic filter to the second image while varying the filter characteristics of the anisotropic filter for each position in the image in accordance with the filter characteristics determined based on the first image.

The present invention in its fourth aspect provides a non-transitory computer readable storage medium storing a program causing a computer to execute the steps of: acquiring data obtained by using an imaging apparatus to capture an image formed by an electromagnetic wave transmitted through an object, as measurement data on the object; generating a first image and a second image that represent information on different physical quantities, from the measurement data; determining, based on the first image, filter characteristics to be set when an anisotropic filter is applied, for each position in the image; and applying the anisotropic filter to the second image while varying the filter characteristics of the anisotropic filter for each position in the image in accordance with the filter characteristics determined based on the first image.

Further features of the present invention will become apparent from the following description of exemplary embodiments with reference to the attached drawings.

DESCRIPTION OF THE EMBODIMENTS

The present invention relates to an image processing apparatus and an image processing method in which an object image is filtered using an anisotropic filter.

The present invention is preferably applicable to imaging apparatuses that can acquire a plurality of types of object images representing different (independent) physical quantities based on measurement data obtained by a single imaging process, regardless of whatever imaging apparatus or imaging method is used for an object. Imaging apparatuses of this type include imaging apparatuses that capture an image formed by electromagnetic waves transmitted through an object, for example, phase imaging apparatuses that image, as an intensity (contrast), a change in wave front (phase) resulting from transmission of electromagnetic waves through the object. Data measured using phase imaging apparatuses include information on a plurality of physical quantities such as differential phase, absorptivity, and scattering (change in amplitude). Electromagnetic waves used for imaging may have any wavelength bands and may be light, X rays, or gamma rays. However, as described below in detail, the filtering technique in the present embodiment can be applied to images with a low SN ratio and are thus particularly preferably applicable to low dose imaging in imaging apparatuses that utilize a radiation such as X rays, gamma rays, neutrons, electron beams. The X rays as used herein refer to electromagnetic waves with an energy of 2 keV or more and 200 keV or less.

As a preferred embodiment of the present invention, an object image obtained by a two-dimensional Talbot X-ray phase imaging apparatus that is a type of two-dimensional differential interferometer will be described by way of example. The filtering technique described below is applicable not only to images obtained by a two-dimensional differential interferometer but also to images obtained by a one-dimensional differential interferometer.

(Imaging System)

Figure 1:
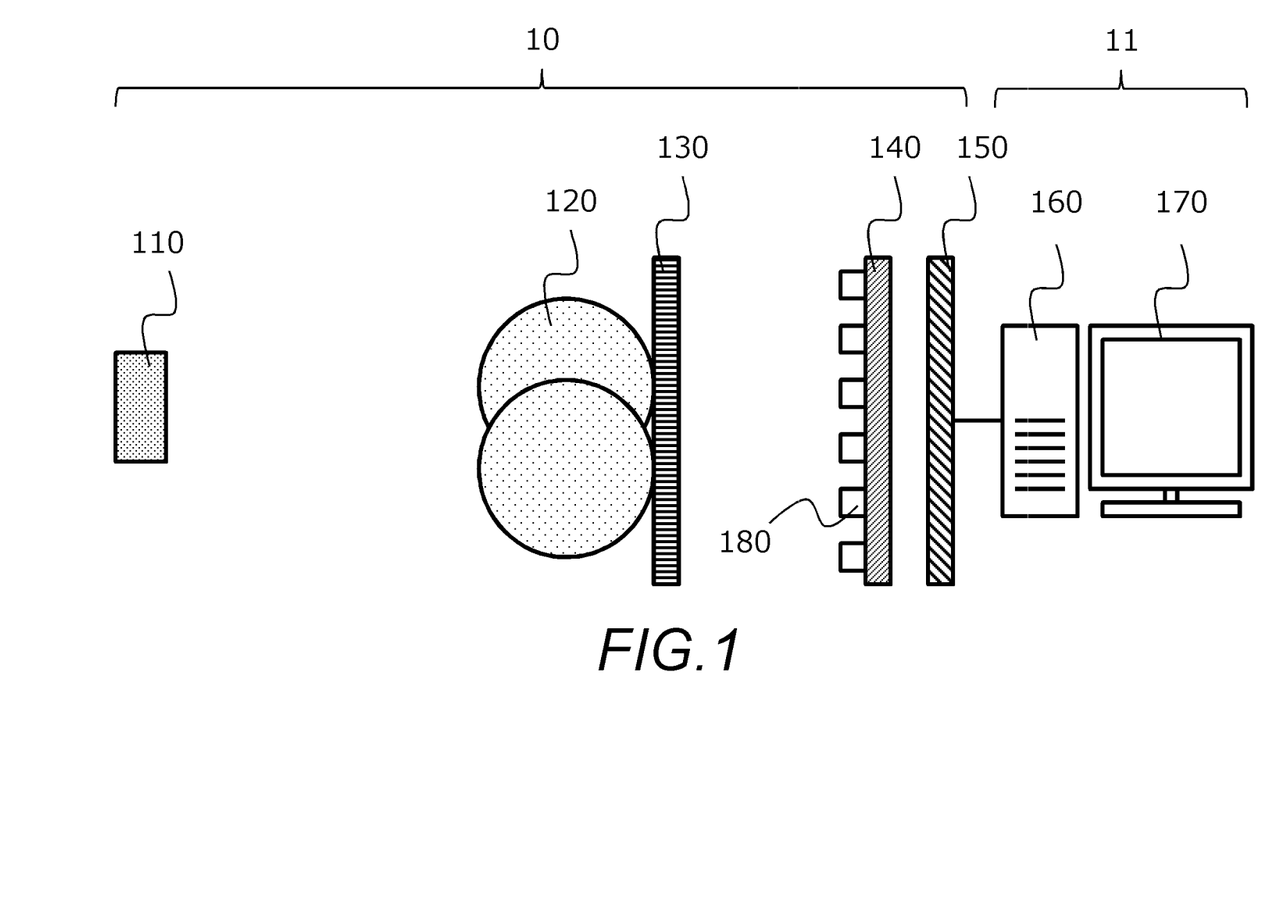
FIG. 1 is a diagram schematically depicting a configuration of an imaging system in an embodiment of the present invention.

FIG. 1 is a diagram depicting a configuration of an imaging system for Talbot X-ray phase imaging. The imaging system includes an imaging apparatus 10 that is an X-ray Talbot interferometer and an image processing apparatus 11 that processes X-ray images acquired by the imaging apparatus 10. The imaging apparatus 10 includes an X-ray source (light source) 110 that generates X rays, a diffraction grating 130 that diffracts X rays, a shield grating 140 that blocks a portion of the X rays, and a detector 150 that detects the X rays. The image processing apparatus 11 has a computing unit (computer) 160 connected to the imaging apparatus 10 and an image display apparatus 170 that displays images based on results of calculations by the computing unit 160.

The computing unit 160 may include a general-purpose computer including hardware resources such as a central processing unit (CPU), a random access memory (RAM), and an auxiliary storage device. Image processing, various calculations, and control described below are implemented by the CPU by loading and executing programs stored in the auxiliary storage device. Some or all of the functions of the computing unit 160 may be provided using such a circuit as an application specific integrated circuit (ASIC).

X rays from the X-ray source 110 are diffracted by the diffraction grating 130 to form an interference pattern 180 with bright portions and dark portions arranged in an arrangement direction, at a position located at a predetermined distance referred to as a Talbot length, from the diffraction grating 130.

A first interference pattern 180 formed through the diffraction grating 130 normally has a period of approximately several micrometers to several tens of micrometers. Thus, the shield grating 140, which has the same period as that of the first interference pattern 180 or a period slightly different from that of the first interference pattern 180, is arranged at a position where the first interference pattern 180 is formed. Then, the first interference pattern 180 and the shield grating 140 allow a moiré pattern to be formed, enabling the period of the interference pattern to be increased to several tens of micrometers or more or to infinity. The period of the moiré pattern can be determined as needed with a phase recovery method used and the pixel size of the detector taken into account. However, in the present embodiment, the period of the moiré pattern is more than twice as large as the pixel size. In the present embodiment, even when the period is large enough to preclude bright portions or dark portions from being formed within an imaging range of the detector 150, an intensity distribution formed by the first interference pattern 180 and the shield grating 140 is referred to as a moiré pattern. The moiré pattern (a pattern with a spatial periodicity) is imaged by the detector 150, which is a two-dimensional image sensor, thus providing a two-dimensional image. This mechanism enables the detector 150 with a resolution of approximately several tens of square micrometers to image an interference pattern with a period of several micrometers to several tens of micrometers. However, if the detector 150 has a sufficiently high spatial resolution, the shield grating 140 may be omitted and the first interference pattern 180 may be directly imaged. An image obtained by the detector 150 and having a periodic pattern is hereinafter referred to as an interference image. Image data on the interference image output from the detector 150 is hereinafter referred to as measurement data.

The diffraction grating 130 may be a phase diffraction grating (phase grating) that periodically modulates the phase of X rays or an amplitude diffraction grating (shield grating) that periodically modulates the amplitude of X rays. However, a phase grating is often used due to a low loss of X rays. As the shield grating 140, a grating with X-ray transmission portions and X-ray shielding portions arranged therein is often used.

During measurement, an object 120 is installed before the diffraction grating 130. X rays are generally transmissive enough to pass through the object 120, and at this time, the phase changes in accordance with the element composition and the density of a substance through which the X rays have been transmitted. The change in phase affects the arrangement of the first interference pattern 180. This also distorts the moiré pattern formed through the shield grating 140. Therefore, information (differential phase) on the change in the phase of X rays caused by the object 120 can be acquired by the computing unit 160 by calculating distortion of the interference image based on a comparison of measurement data obtained when the object 120 is not present and measurement data obtained when the object 120 is installed. When X rays are transmitted through the object 120, the energy of X rays is partly absorbed by the object 120. Absorptivity in this case varies according to the element composition of the tissue. Therefore, information on the absorption of X rays by the object 120 can be acquired by the computing unit 160 by calculating an intensity ratio based on a comparison of the measurement data obtained when the object 120 is not present and the measurement data obtained when the object 120 is installed. When fine structures (for example, fibrous tissues or fine calcified masses) are densely packed in any internal part of the object 120, small-angle scattering occurs in that part, changing the amplitude of X rays measured. Therefore, information on the small-angle scattering of X rays caused by the object 120 can be acquired by the computing unit 160 by analyzing a change in amplitude based on a comparison of the measurement data obtained when the object 120 is not present and the measurement data obtained when the object 120 is installed. As a result, information on three independent physical quantities, differential phase, absorptivity, and small-angle scattering, can be acquired based on the measurement data obtained by the detector 150. Imaged two-dimensional distributions of the information on the physical quantities are referred to as a differential phase image, an absorption image, and a scattering image (or a visibility contrast image), respectively. The X-ray phase imaging apparatus has been described in brief. Integration of information on the differential phase allows information on the phase to be acquired. However, the differential phase and the phase are not independent physical quantities.

COMPARATIVE EXAMPLES

First, as a comparative example, an example will be described which is a simple combination of an image processing method utilizing inverse Riesz transform and disclosed in US Patent Application Publication No. US 2014/0153692 (hereinafter referred to as Conventional Method 1) and the anisotropic filtering method disclosed in International Publication No. WO 2010/034968 (hereinafter referred to as Conventional Method 2).

Figure 2A:
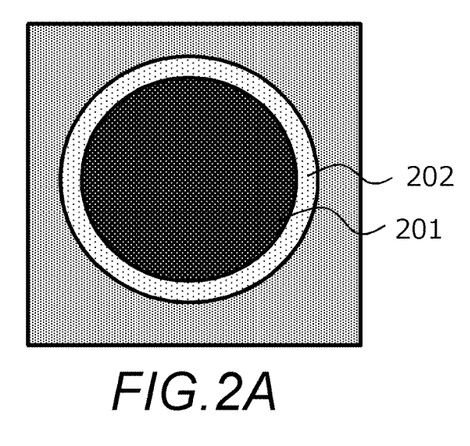
FIGS. 2A to 2D are diagrams depicting a configuration of an object and examples of differential phase images and an inverse Riesz image.

The specification assumes, as an object, a phantom that simulates an actual living tissue. Based on an interference image (moiré image) obtained by computer simulation, the following image processing is executed. FIG. 2A depicts the structure of the phantom. The phantom is shaped to have a spherical double structure. A first layer 201 is a structure with a high absorptivity. For example, in terms of living tissues, a living tissue corresponding to a bone is represented by the first layer 201. A second layer 202 is a structure with a low absorptivity and a low refractive index. In terms of living tissues, a cartilage in the above-described living tissue is simulated by the second layer 202. Physical constants for the absorptivity and the refractive index were set to values in accordance with the above-described situation. The phantom was set to 2 cm in size. To reproduce an image of a cartilage in another living tissue such as the skin tissue or a muscle tissue, the phantom was assumed to be installed in water. This reduces a difference in refraction between the first layer 201 and the second layer 202 to decrease the contrast of a phase image.

Figure 2B:
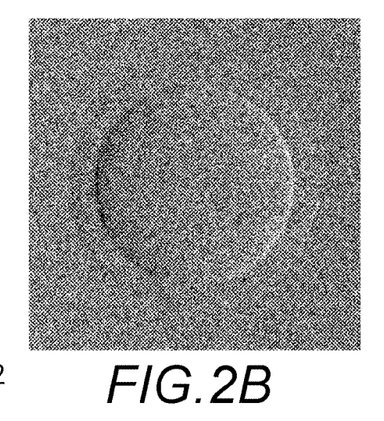
Figure 2C:
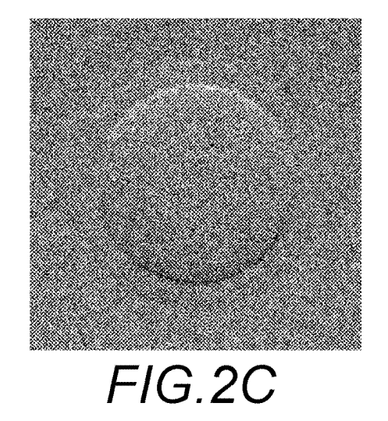
Figure 2D:
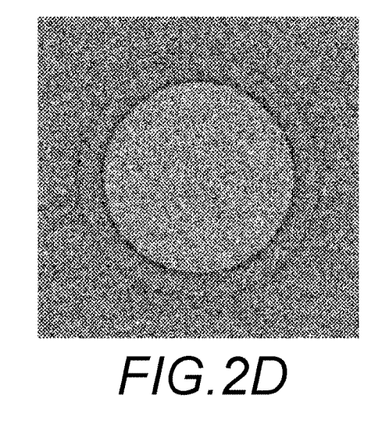

An interference image observed when the phantom in FIG. 2A is imaged by the imaging apparatus 10 in FIG. 1 is determined by simulation. FIG. 2B and FIG. 2C illustrate examples of differential phase images generated based on the interference image. FIG. 2B depicts a differential phase image in an X axis direction, and FIG. 2C depicts a differential phase image in a Y axis direction. An exposure dose was assumed to be 5 mGy. This exposure dose is standard or slightly high for medical X-ray imaging. A central portion of the phantom that corresponds to the bone is contrasted, whereas the contrast of an end of the cartilage is substantially invisible. FIG. 2D depicts an image resulting from application of Conventional Method 1 to the differential phase images (the image is hereinafter referred to as an inverse Riesz image). Compared to the cartilage end in the differential phase images in FIG. 2B and FIG. 2C, the cartilage end in the inverse Riesz image is slightly visualized. However, the visualization is not sufficient. For example, in medical applications, confirmation of the presence of the cartilage may not be sufficient, and the thickness of the cartilage may be an important criterion for diagnosis. FIG. 2D allows the presence of the cartilage to be confirmed, but it is difficult to accurately measure the thickness using FIG. 2D. Consequently, some combinations of an object with imaging conditions make the image obtained by Conventional Method 1 insufficient for diagnosis.

Figure 3A:
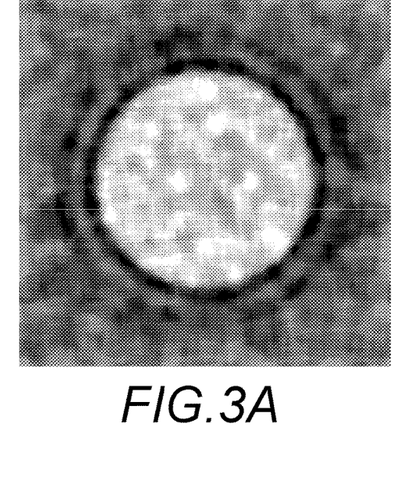
FIG. 3A and FIG. 3B are diagrams illustrating filtering results in comparative examples.

Now, results of application of filter-based noise reduction to the inverse Riesz image in FIG. 2D will be described. FIG. 3A illustrates results of application of an isotropic filter to the inverse Riesz image in FIG. 2D. The filter was 25×25 pixels in size. A median filter was used for the smoothing technique. As a result, the contrast was slightly improved at the cartilage portion but was nonuniform. Furthermore, a portion representing an edge of the cartilage is wide, hindering quantitation during thickness measurement and making the thickness measurement difficult.

Figure 3B:
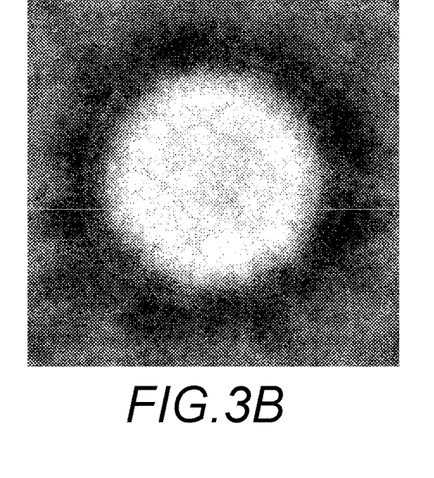

FIG. 3B illustrates results of application of Conventional Method 2 to the inverse Riesz image in FIG. 2D. An anisotropic filter with a size of 81×7 pixels was used. The direction of the anisotropic filter was calculated based on differential phases in the X axis direction and the Y axis direction, which are primary information acquired by two-dimensional Talbot X-ray phase imaging. Aligning two differential phases with each other allows a vector for a phase gradient to be set, and thus, the same median filter as described above was applied with the direction of short sides of the anisotropic filter aligned with the direction of the vector. As a result, the image was generally obscure, in particular, the contrast of the edge of the cartilage disappeared.

The above-described results indicate that application of the simple combination of Conventional Methods 1 and 2 to the sample makes the SN ratio insufficient or reduces the SN ratio.

(Embodiment)

Now, an embodiment of image processing executed by the image processing apparatus 11 in the present embodiment will be described. In the present embodiment, filter characteristics (direction, shape, and the like) of the applied anisotropic filter are not determined on the differential phase but on an absorption image generated from the same measurement data. For the bone portion, the absorption image exhibits a higher contrast than the differential phase image and the inverse Riesz image. Thus, the direction of the filter is determined using an edge direction of the structure in the absorption image as auxiliary information. As described above, a feature of the present embodiment is that an image used to determine the filter characteristics (first image) and an image to which the filter process is applied (second image) are those of the images generated from the same measurement data which represent information on different physical quantities. Any combination of the first image and the second image is possible, but the first image preferably has a higher SN ratio than the second image (the structure desired to be observed has a high contrast). By determining the filter characteristics using the first image, which has a higher SN ratio than the second image to which the filter is applied, the filter characteristics can be more appropriately determined than when determining the filter characteristics using the second image, allowing values close to the information on the object to be obtained.

Figure 4:
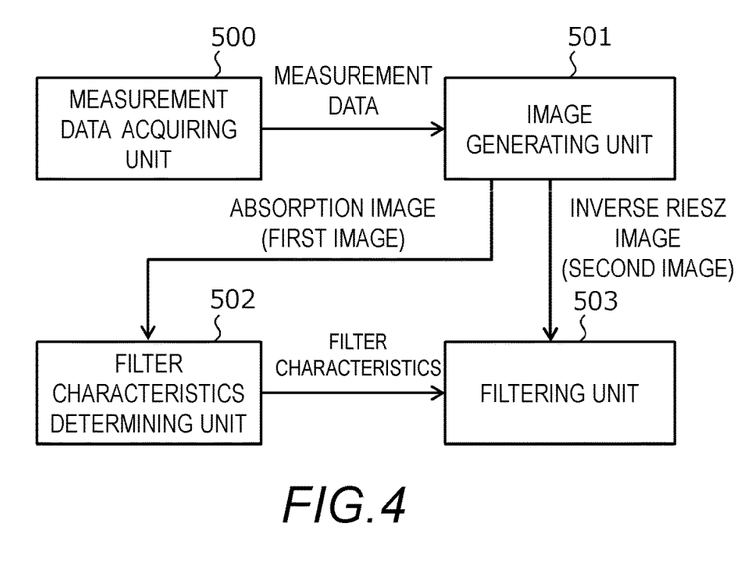
FIG. 4 is a functional block diagram for a filtering process in an embodiment.

FIG. 4 is a functional block diagram for the filtering process provided by the image processing apparatus 11. The image processing apparatus 11 has, as functions thereof, a measurement data acquiring unit 500, an image generating unit 501, a filter characteristics determining unit 502, and a filtering unit 503. The measurement data acquiring unit 500 is a function to acquire measurement data on the object 120 obtained by the imaging apparatus 10. The image generating unit 501 is a function to analyze the measurement data to generate images such as an absorption image, a differential phase image, a scattering image, and an inverse Riesz image. The filter characteristics determining unit 502 is a function to determine the filter characteristics of an anisotropic filter. The filtering unit 503 is a function to apply the anisotropic filter to the image in accordance with the filter characteristics determined by the filter characteristics determining unit 502. The anisotropic filter is a filter having directional dependence to smooth the image along one direction. The present embodiment uses an anisotropic filter that is 81×7 pixels in size and that has a smoothing effect (noise reduction effect) along the direction of short sides of the filter. These functions are implemented by the computing unit 160 by executing needed programs.

Figure 5:
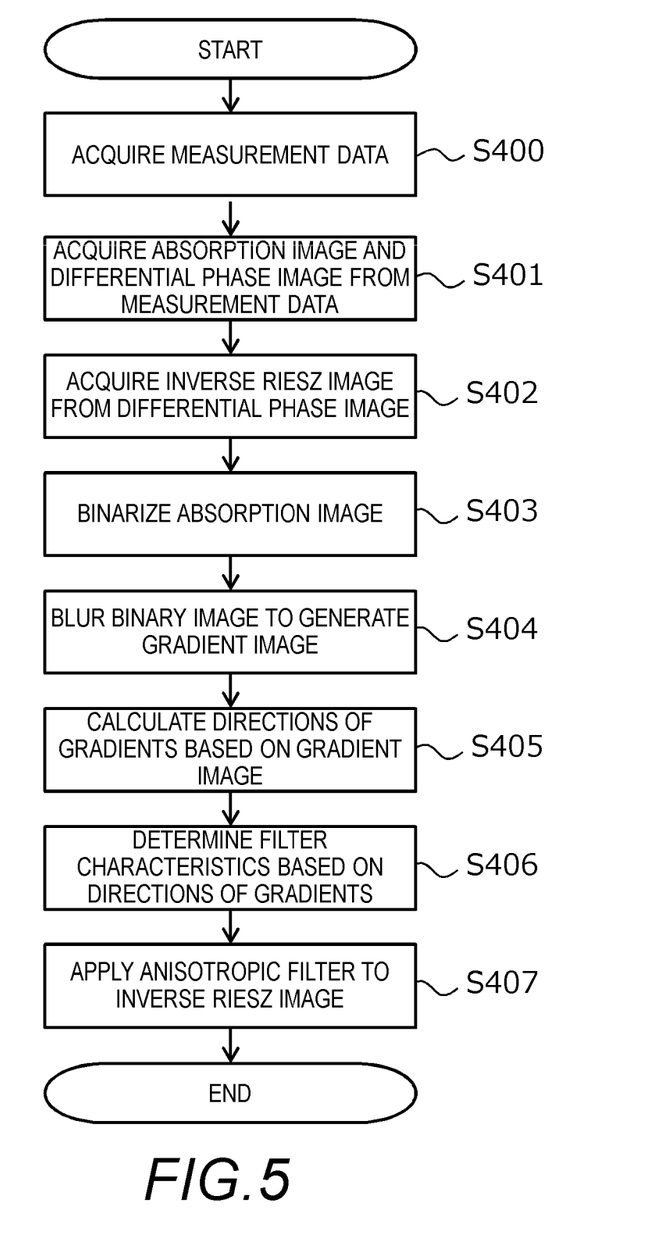
FIG. 5 is a flowchart illustrating a flow of the filtering process in the embodiment.

With reference to a flowchart in FIG. 5, a flow of the filtering process provided by the image processing apparatus 11 will be described. First, the measurement data acquiring unit 500 acquires the measurement data obtained by the imaging apparatus 10 (step S400). At this time, the measurement data may be acquired in real time from the imaging apparatus 10 or the measurement data previously obtained and saved in a storage or the like may be loaded. Then, the image generating unit 501 analyzes the measurement data to generate an absorption image, a differential phase image in the X axis direction, and a differential phase image in the Y axis direction (step S401). The image generating unit 501 then uses the inverse Riesz transform to convert the differential phase images into an inverse Riesz image (step S402). If an absorption image, differential phase images, an inverse Riesz image, and the like have already been generated and saved in the storage or the like, the image data may be loaded in steps S401 and S402. For the inverse Riesz transform, the method disclosed in US Patent Application Publication No. US 2014/0153692 is utilized. Thus, detailed description of the inverse Riesz transform is omitted.

Figure 6A:
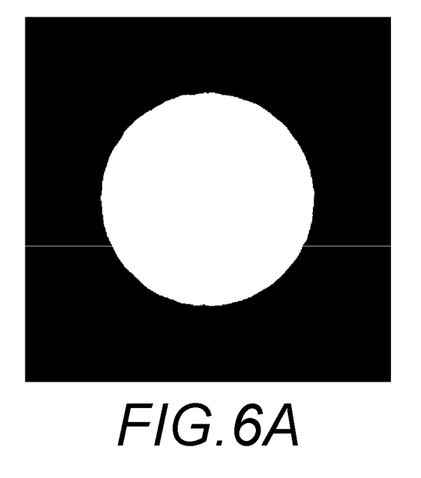
FIGS. 6A to 6D are diagrams illustrating filtering effects in the embodiment.

Then, the filter characteristics determining unit 502 uses the absorption image to extract an edge direction (a tangential direction of a boundary) of a structure in the image (for example, a bone). The filter characteristics determining unit 502 then determines a normal direction orthogonal to the edge direction. To achieve this, the filter characteristics determining unit 502 may calculate the direction of the gradient of a pixel value in the image for each position in the image. In the present embodiment, the filter characteristics determining unit 502 first binarizes the absorption image (step S403). The binarization is an operation of converting the value of each pixel in the image into 1 (True) or 0 (False). In the present embodiment, the binarization is performed by determining whether or not each pixel value in the absorption image is larger than a threshold. The threshold may be a fixed value or may be dynamically (adaptively) determined. A median filter is preferably applied to a binary image as needed. This is an operation of more definitely separating the bone area from the other areas. FIG. 6A depicts a binary image thus acquired. The bone area can be extracted by adjusting the threshold and parameters for the median filter (a blank area in FIG. 6A is the bone area).

Figure 6B:
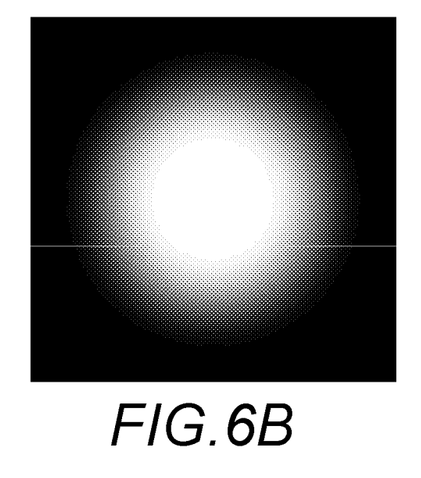

Then, the filter characteristics determining unit 502 blurs the binary image by convolution (step S404). In the present embodiment, the binary image is convoluted using a Gaussian filter. FIG. 6B depicts the resultant image (hereinafter referred to as a gradient image). The process in step S404 is intended to form a continuous gradient for pixel values using the edge of the structure in the image (for example, the boundary of the bone) as a ridge. Using such a gradient image facilitates appropriate setting of the filter characteristics at each position in the image. In this case, the image is preferably blurred to the four corners thereof, and the blur is preferably isotropic.

Figure 6C:
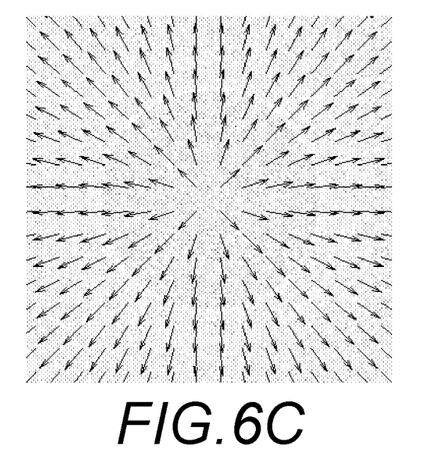

Then, based on the gradient image, the filter characteristics determining unit 502 calculates the gradient of each position in the image (step S405). In the present embodiment, only the direction of the gradient is acquired. However, the magnitude of the gradient may also be acquired and utilized for determining the filter characteristics. FIG. 6C depicts the directions of the gradients calculated based on the gradient image in FIG. 6B. Each arrow in FIG. 6C depicts the direction of the gradient. FIG. 6C illustrates that gradient vectors are directed outward with respect to the center of the figure. This indicates that the boundary of the bone has successfully been determined over the entire area of the image, allowing the normal direction of the boundary to be determined. This object is shaped like a sphere. However, even when the image of the bone has a complicated boundary line, using the present technique allows determination of the normal direction of the boundary. The filter characteristics determining unit 502 determines the filter characteristics for each position in the image such that the direction of the gradient is parallel to the direction of the anisotropic filter (direction of short sides) (step S406).

Then, the filtering unit 503 applies the anisotropic filter to all the pixels in the inverse Riesz image while varying the filter characteristics (the direction of the filter in the present embodiment) for each position in the image in accordance with the filter characteristics determined in step S406 (step S407). Consequently, noise reduction is performed along the directions of the gradients.

Figure 6D:
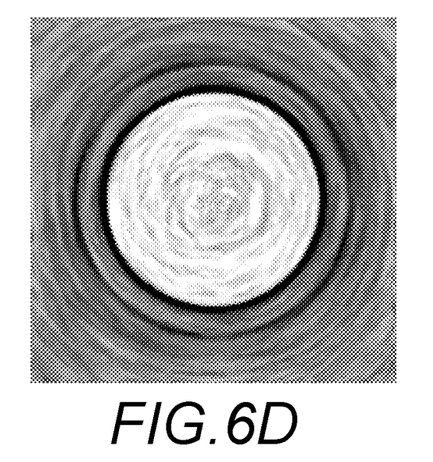

FIG. 6D illustrates results of the noise reduction performed on the inverse Riesz image in FIG. 2D along the directions depicted in FIG. 6C (in this case using a median filter). Compared to the images in the comparative examples in FIG. 3A and FIG. 3B, the image in FIG. 6D clearly depicts the shape of the cartilage. The portion of the image that depicts the edge of the cartilage is narrow, indicating that the image is suitable for determining how far the edge position of the cartilage is located from a bone surface (boundary), that is, determining the thickness of the cartilage.

Figure 7A:
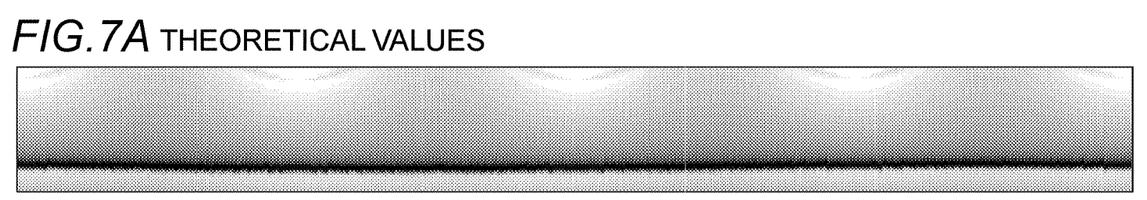
FIGS. 7A to 7D are diagrams illustrating a comparison between results of the embodiment and results of the comparative examples and theoretical values.
Figure 7B:
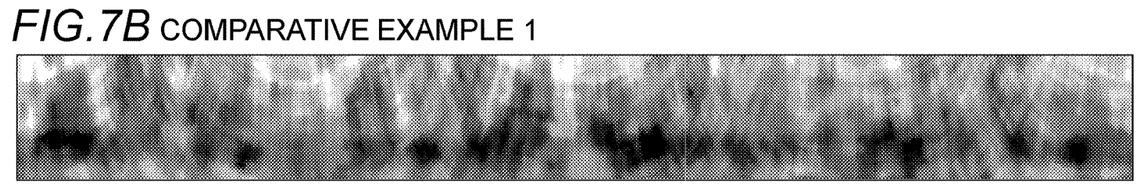
Figure 7C:
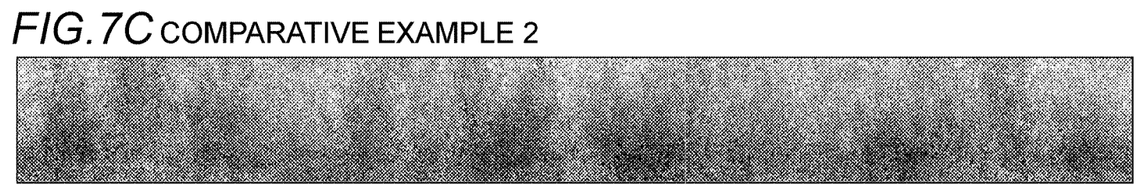
Figure 7D:
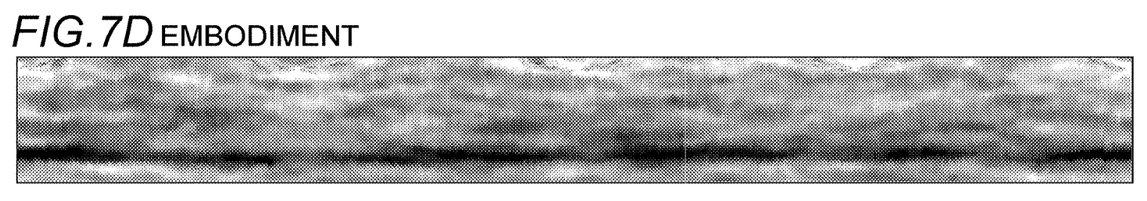

FIGS. 7A to 7D are diagrams illustrating a quantitative comparison of the effects of the present embodiment with effects of Comparative Example. FIGS. 7A to 7D are diagrams depicting a neighborhood area of the cartilage cut out into a donut shape, which is then mapped to a rectangular shape. FIG. 7A illustrates theoretical values. FIGS. 7B to 7D are images cut out from the images in FIG. 3A (Comparative Example 1), FIG. 3B (Comparative Example 2), and FIG. 6D (Embodiment), respectively. The image obtained in the present embodiment (FIG. 7D) clearly depicts the edge of the cartilage at substantially the same position as that in the theoretical values (FIG. 7A).

Figure 8:
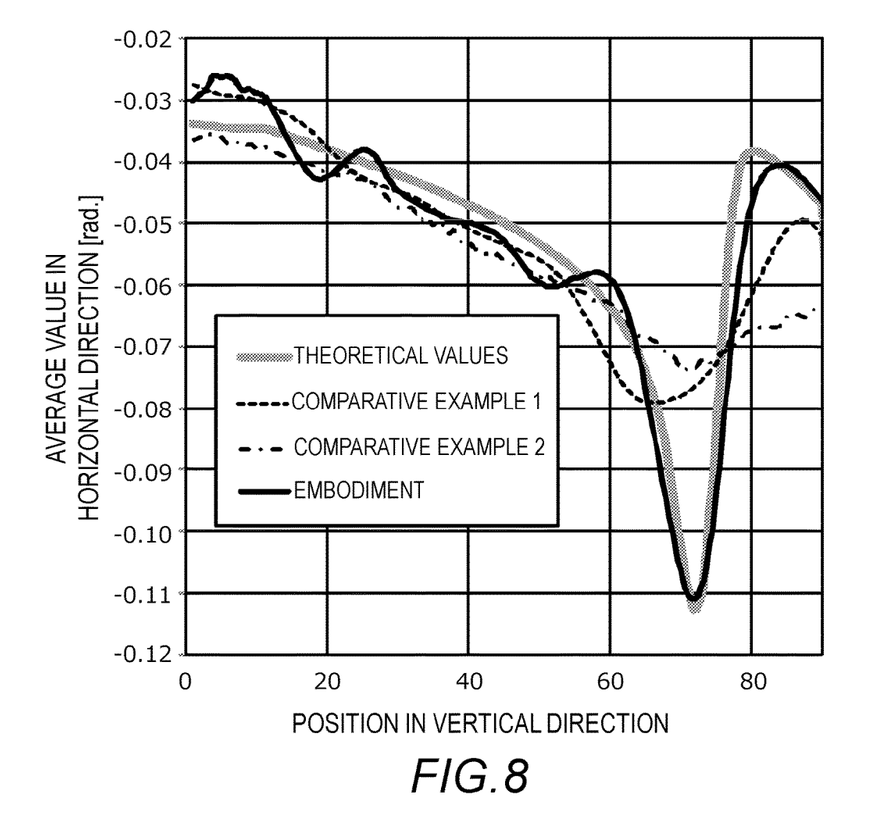
FIG. 8 is a diagram illustrating a comparison between results of the embodiment and results of the comparative examples and the theoretical values.

FIG. 8 is a plot of average values in the horizontal direction in the images in FIGS. 7A to 7D. For vertical positions, upper ends of the sheets of FIGS. 7A to 7D are set to zero. Profiles in Comparative Example 1 and Comparative Example 2 deviate from a profile based on the theoretical values. The position of the minimal value in the profile (the position presumed to be the edge of the cartilage) in each of Comparative Example 1 and Comparative Example 2 also significantly deviates from the position of the minimal value in the profile based on the theoretical values. FIG. 8 indicates, in contrast, that the present embodiment has successfully provided a profile close to the theoretical values and enables more quantitative image processing than the comparative examples.

Applied Example

The filtering technique according to the present invention is applicable in various forms. For example, in the above-described embodiment, the noise reduction is performed, with reference to the absorption image, on the inverse Riesz image acquired based on the differential phase. However, the image to which the anisotropic filter is applied may be a differential phase image, a phase image resulting from integration of differential phase images, a Laplacian image resulting from differentiation of the differential phase images, or any other image. When a phase contrast is higher than an absorption contrast, the process in the present embodiment may be reversed. That is, the filter characteristics may be determined based on a differential phase image or an image resulting from processing of the differential phase image (inverse Riesz image or phase image), and the anisotropic filter may be applied to an absorption image. These techniques may also be used for noise reduction for a scattering image (moiré amplitude image), which can also be acquired by phase imaging. Since the X-ray phase imaging allows an absorption image, a differential phase image, or a scattering image to be acquired as a primary image, various aspects are possible in which, to subject any of these images or another image created from the these images to image processing, yet another image is created and utilized. The present technique can be applied to one-dimensional X-ray phase imaging in addition to the two-dimensional X-ray phase imaging. The present technique can be also applied to imaging apparatuses other than Talbot interferometers. In the above-described embodiment, the first image is blurred by binarization and convolution in order to acquire gradient information on the first image. However, the method for acquiring the gradient information is not limited to this, and any known method may be used. Results similar to those of the above-described embodiment may be produced by using the gradient information acquired from the first image to determine the anisotropic filter applied to the second image.

In the above-described embodiment, the anisotropic filter has a fixed shape formed of 81×7 pixels. The filter shape is not limited to this. The shape of the anisotropic filter may be varied according to conditions or a location in the image, or a square filter may be used. For example, for the filter characteristics, only the direction of the filter is changed in the present embodiment. However, the shape or size of the anisotropic filter, a coefficient for the anisotropic filter, or the like may be changed according to the magnitude of the gradient. Furthermore, instead of the median filter, an averaging filter based on a general Gaussian filter or any of various other filters may be used.

Specific implementation of the above-described image processing apparatus may be based on either software (program) or hardware. For example, the processes may be implemented by storing a computer program in a computer (a microcomputer, a CPU, an MPU, an FPGA, or the like) built in the image processing apparatus and allowing the computer to execute the computer program. A dedicated processor such as an ASIC is preferably provided which implements all or some of the processes of the present invention using logic circuits. The present invention is also applicable to a server in a cloud environment.

The present invention may also be implemented by, for example, a method including steps executed by a computer of a system or an apparatus that accomplishes the functions of the embodiment described above by loading and executing programs recorded in a storage device. To accomplish this object, the program is provided to the computer, for example, through a network or from various types of recording media each of which can serve as the storage device (in other words, computer readable recording media holding data in a non-transitory manner). Therefore, the scope of the present invention includes any of the above-described computer (including devices such as a CPU and an MPU), the above-described method, the above-described program (including program code and a program product), and a computer readable recording medium holding the program in a non-transitory manner.

The present invention can produce reliable filter results when an anisotropic filter is applied to an object image (particularly an image with a low SN ratio).

Other Embodiments

Embodiment (s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment (s) and/or that includes one or more circuits (e.g., application specific integrated circuit (ASIC)) for performing the functions of one or more of the above-described embodiment (s), and by a method performed by the computer of the system or apparatus by, for example, reading out and executing the computer executable instructions from the storage medium to perform the functions of one or more of the above-described embodiment (s) and/or controlling the one or more circuits to perform the functions of one or more of the above-described embodiment (s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-145042, filed on Jul. 22, 2015, which is hereby incorporated by reference herein in its entirety.

What is claimed is:

1. An image processing apparatus comprising:
a measurement data acquiring unit that acquires measurement data of an object, the measurement data being obtained by using an imaging apparatus to capture an image formed by an electromagnetic wave transmitted through the object;
an image generating unit that generates, from the measurement data, a first image, which represents first unique two-dimensional information based on a first unique physical quantity, and a second image, which represents second unique two-dimensional information based on a second unique physical quantity;
a filter characteristics determining unit that determines, based on the first image, filter characteristics of an anisotropic filter; and
a filtering unit that applies the anisotropic filter having the determined filter characteristics to the second image, in each position in the second image.

2. The image processing apparatus according to claim 1, wherein the filter characteristics include a direction of the anisotropic filter.

3. The image processing apparatus according to claim 2, wherein the anisotropic filter smoothes the image along the direction of the anisotropic filter.

4. The image processing apparatus according to claim 2, wherein the filter characteristics determining unit determines the filter characteristics of the anisotropic filter for each position in the image such that an edge direction of a structure included in the first image is orthogonal to the direction of the anisotropic filter.

5. The image processing apparatus according to claim 2, wherein the filter characteristics determining unit calculates a direction of a gradient of a pixel value in the first image for each position in the image to determine the filter characteristic of the anisotropic filter for each position in the image such that the direction of the gradient is parallel to the direction of the anisotropic filter.

6. The image processing apparatus according to claim 1, wherein the first image has a higher signal to noise ratio than the second image.

7. The image processing apparatus according to claim 1, wherein the imaging apparatus is a phase imaging apparatus.

8. The image processing apparatus according to claim 7, wherein the electromagnetic wave is a radiation.

9. The image processing apparatus according to claim 8, wherein the radiation is an X ray.

10. The image processing apparatus according to claim 7, wherein the first image is an image that represents information on absorption of the electromagnetic wave by the object.

11. The image processing apparatus according to claim 7, wherein the second image is an image that represents information on a change in a phase of the electromagnetic wave caused by the object.

12. An imaging system comprising:
an imaging apparatus that captures an image formed by an electromagnetic wave transmitted through an object to output measurement data of the object; and
the image processing apparatus according to claim 1 that applies image processing to the measurement data obtained by the imaging apparatus.

13. An image processing method comprising the steps of:
causing a computer to acquire measurement data of an object, the measurement data being obtained by using an imaging apparatus to capture an image formed by an electromagnetic wave transmitted through object;
causing the computer to generate, from the measurement data, a first image, which represents first unique two-dimensional information based on a first unique physical quantity, and a second image, which represents second unique two-dimensional information based on a second unique physical quantity;
causing the computer to determine, based on the first image, filter characteristics of an anisotropic filter; and
causing the computer to apply the anisotropic filter having the determined filter characteristics to the second image, in each position in the second image.

14. The image processing method according to claim 13, wherein the electromagnetic wave is an X ray.

15. A non-transitory computer readable storage medium storing a program causing a computer to execute steps comprising:
acquiring measurement data of an object, the measurement data being obtained by using an imaging apparatus to capture an image formed by an electromagnetic wave transmitted through the object;
generating, from the measurement data, a first image, which represents first unique two-dimensional information based on a first unique physical quantity, and a second image, which represents second unique two-dimensional information based on a second unique physical quantity;
determining, based on the first image, filter characteristics of an anisotropic filter; and
applying the anisotropic filter having the determined filter characteristics to the second image, in each position in the second image.

* * * * *